United States Patent
Piha et al.

(10) Patent No.: US 9,700,733 B2
(45) Date of Patent: Jul. 11, 2017

(54) WEARABLE CARDIAC DEFIBRILLATOR SYSTEM WITH IMPEDANCE MEASUREMENT CIRCUIT TO CONTROL CONDUCTIVE FLUID DEPLOYMENT

(71) Applicant: West Affum Holdings Corp., Grand Cayman (KY)

(72) Inventors: Daniel Ralph Piha, Bellevue, WA (US); Joseph Leo Sullivan, Kirkland, WA (US); Phillip Dewey Foshee, Jr., Woodinville, WA (US); Daniel Peter Finch, Bothell, WA (US); Isabelle Banville, Newcastle, WA (US); Laura Marie Gustavson, Redmond, WA (US); Kenneth Frederick Cowan, Kirkland, WA (US); Richard C. Nova, Seattle, WA (US); Robert Reuben Buchanan, Bothell, WA (US); Krystyna Szul, Seattle, WA (US); Gregory T. Kavounas, Bellevue, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

(21) Appl. No.: 15/384,101

(22) Filed: Dec. 19, 2016

(65) Prior Publication Data

US 2017/0106198 A1    Apr. 20, 2017

Related U.S. Application Data

(60) Division of application No. 15/135,462, filed on Apr. 21, 2016, now abandoned, which is a continuation of
(Continued)

(51) Int. Cl.
  *A61N 1/39* (2006.01)
  *A61N 1/04* (2006.01)
  *A61N 1/362* (2006.01)

(52) U.S. Cl.
  CPC .......... *A61N 1/3918* (2013.01); *A61N 1/046* (2013.01); *A61N 1/0496* (2013.01); *A61N 1/3625* (2013.01); *A61N 1/3987* (2013.01)

(58) Field of Classification Search
  CPC .... A61N 1/046; A61N 1/0472; A61N 1/0492; A61N 1/39; A61N 1/3993; A61N 1/3918;
  (Continued)

(56) References Cited

U.S. PATENT DOCUMENTS 3,724,455 A    4/1973 Unger
4,583,524 A    4/1986 Hutchins
(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Rex R Holmes
(74) *Attorney, Agent, or Firm* — Kavounas Patent Law Office, PLLC

(57) ABSTRACT

In embodiments, a wearable cardiac defibrillator system includes an energy storage module configured to store a charge. Two electrodes can be configured to be applied to respective locations of a patient. One or more reservoirs can store one or more conductive fluids. Respective fluid deploying mechanisms can be configured to cause the fluids to be released from one or more of the reservoirs, which decreases the impedance at the patient location, and decreases discomfort for the patient. In some embodiments
(Continued)

WEARABLE DEFIBRILLATOR SYSTEM an impedance is sensed between the two electrodes, and the stored charge is delivered when the sensed impedance meets a discharge condition. In some embodiments, different fluids are released for different patient treatments. In some embodiments, fluid release is controlled to be in at least two doses, with an intervening pause.

31 Claims, 13 Drawing Sheets

Related U.S. Application Data application No. 14/161,269, filed on Jan. 22, 2014, now Pat. No. 9,345,898.

(60) Provisional application No. 61/841,222, filed on Jun. 28, 2013, provisional application No. 61/755,919, filed on Jan. 23, 2013.

(58) Field of Classification Search
CPC .. A61N 1/3925; A61N 1/3968; A61N 1/0484; A61N 1/327; A61N 1/3987
See application file for complete search history.

(56) References Cited

U.S. PATENT DOCUMENTS

| | | | |
|---|---|---|---|
| 4,619,265 A | 10/1986 | Morgan et al. | |
| 4,928,690 A * | 5/1990 | Heilman | A61N 1/39 600/509 |
| 5,078,134 A | 1/1992 | Heilman et al. | |
| 5,228,449 A | 7/1993 | Christ et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,529,875 B1 | 3/2003 | Nakajima | |
| 7,559,902 B2 | 7/2009 | Ting et al. | |
| 7,865,238 B2 | 1/2011 | Brink | |
| 7,870,761 B2 | 1/2011 | Valentine et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,965,500 B2 | 2/2015 | Macho et al. | |
| 9,131,901 B2 | 9/2015 | Volpe et al. | |
| 9,132,267 B2 | 9/2015 | Kaib | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2010/0298899 A1* | 11/2010 | Donnelly | A61B 5/02055 607/6 |
| 2011/0288604 A1 | 11/2011 | Kaib et al. | |
| 2011/0288605 A1 | 11/2011 | Kaib et al. | |
| 2012/0144551 A1 | 6/2012 | Guldalian | |
| 2012/0150008 A1* | 6/2012 | Kaib | A61B 5/04 600/372 |
| 2012/0158075 A1 | 6/2012 | Kaib et al. | |
| 2012/0265265 A1 | 10/2012 | Razavi et al. | |
| 2012/0310315 A1 | 12/2012 | Savage et al. | |
| 2014/0378812 A1 | 12/2014 | Saroka et al. | |

OTHER PUBLICATIONS

LIFECOR LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.

* cited by examiner

WEARABLE DEFIBRILLATOR SYSTEM

COMPONENTS

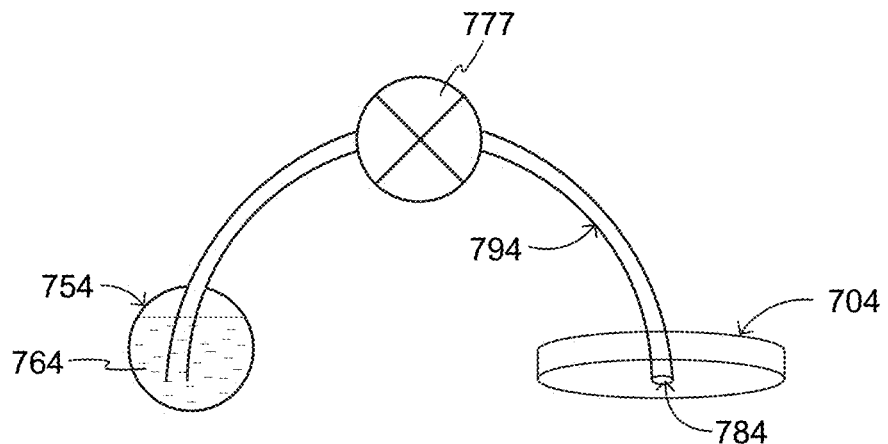
FIG. 7  *WITH PUMP FOR FLUID*
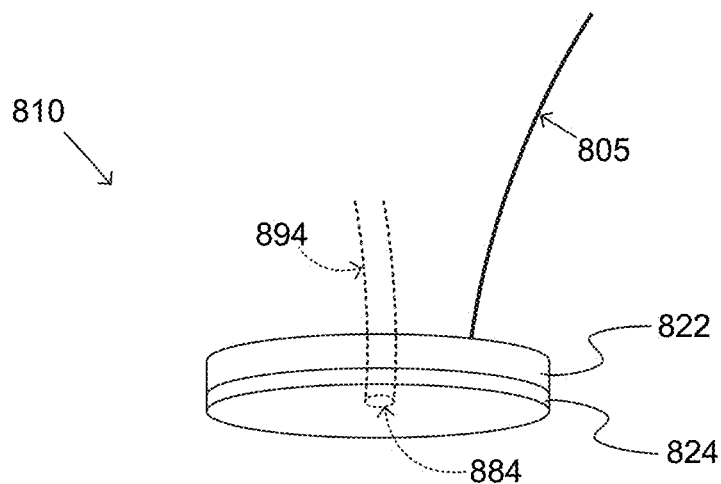
FIG. 8  *ELECTRODE WITH FLUID RETENTION STRUCTURE*

SENSED IMPEDANCE AS
ELECTROLYTE FLUID IS RELEASED

FIG. 13   *METHODS*

METHODS

WEARABLE CARDIAC DEFIBRILLATOR SYSTEM WITH IMPEDANCE MEASUREMENT CIRCUIT TO CONTROL CONDUCTIVE FLUID DEPLOYMENT

CROSS REFERENCE TO RELATED PATENT APPLICATIONS

This patent application is a divisional of copending U.S. patent application Ser. No. 15/135,462, filed on Apr. 21, 2016, which in turn is a continuation of U.S. patent application Ser. No. 14/161,269, filed on Jan. 22, 2014, and issued as U.S. Pat. No. 9,345,898 on May 24, 2016, and which in turn claims priority from U.S. Provisional Patent Application Ser. No. 61/755,919, filed on Jan. 23, 2013, and also from U.S. Provisional Patent Application Ser. No. 61/841,222, filed on Jun. 28, 2013, the disclosures of which are hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest ("SCA"). SCA can lead to death very quickly, e.g. within 10 minutes, unless treated in the interim.

Some people have an increased risk of SCA. People at a higher risk include individuals who have had a heart attack, or a prior SCA episode. These people receive the recommendation to receive an Implantable Cardioverter Defibrillator ("ICD"). An ICD continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardiac defibrillator ("WCD") system. A wearable defibrillator system typically includes a harness, vest, or other garment for wearing by the patient. The system includes a defibrillator and external electrodes, which are attached on the inside of the harness, vest, or other garment. When the person wears the system, the external electrodes may then make good electrical contact with the person's skin, and therefore can help monitor the person's ECG. If a shockable heart arrhythmia is detected, then the defibrillator delivers the appropriate electric shock through the person's body, and thus through the heart.

A challenge occurs at the electrode/skin interface. The challenge occurs if there were to be a gelled electrode, because the gel can dry out and irritate the person's skin, while undesirably increasing the impedance.

BRIEF SUMMARY

The present description gives instances of wearable cardiac defibrillator systems, software, and methods, the use of which may help overcome problems and limitations of the prior art.

In embodiments, a wearable cardiac defibrillator system includes an energy storage module configured to store a charge. Two electrodes can be configured to be applied to respective locations of a patient. One or more reservoirs can store one or more conductive fluids. Respective fluid deploying mechanisms can be configured to cause the fluids to be released from one or more of the reservoirs, which decreases the impedance at the patient location, and decreases discomfort for the patient. In some embodiments an impedance is sensed between the two electrodes, and the stored charge is delivered when the sensed impedance meets a discharge condition. In some embodiments, different fluids are released for different patient treatments. In some embodiments, fluid release is controlled to be in at least two doses, with an intervening pause.

An advantage over the prior art is that the release of fluid is controlled in certain situations, and patient discomfort from irritation or electric shock can be minimized.

These and other features and advantages of this description will become more readily apparent from the following Detailed Description, which proceeds with reference to the drawings, in which:

BRIEF DESCRIPTION OF THE DRAWINGS

FIG. 7 is a diagram of a pump configured to pumping fluid from a reservoir to a patient location, according to an embodiment.

FIG. 8 is a diagram of an electrode with an attached fluid retention structure, according to embodiments.

DETAILED DESCRIPTION

As has been mentioned, the present description is about wearable cardiac defibrillators, software, and methods. Embodiments are now described in more detail.

A wearable defibrillator system made according to embodiments has a number of components. One of these components is a support structure, which is configured to be worn by the patient. The support structure can be any structure suitable for wearing, such as a harness, a vest, one or more belts, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can also be other examples.

Figure 1:
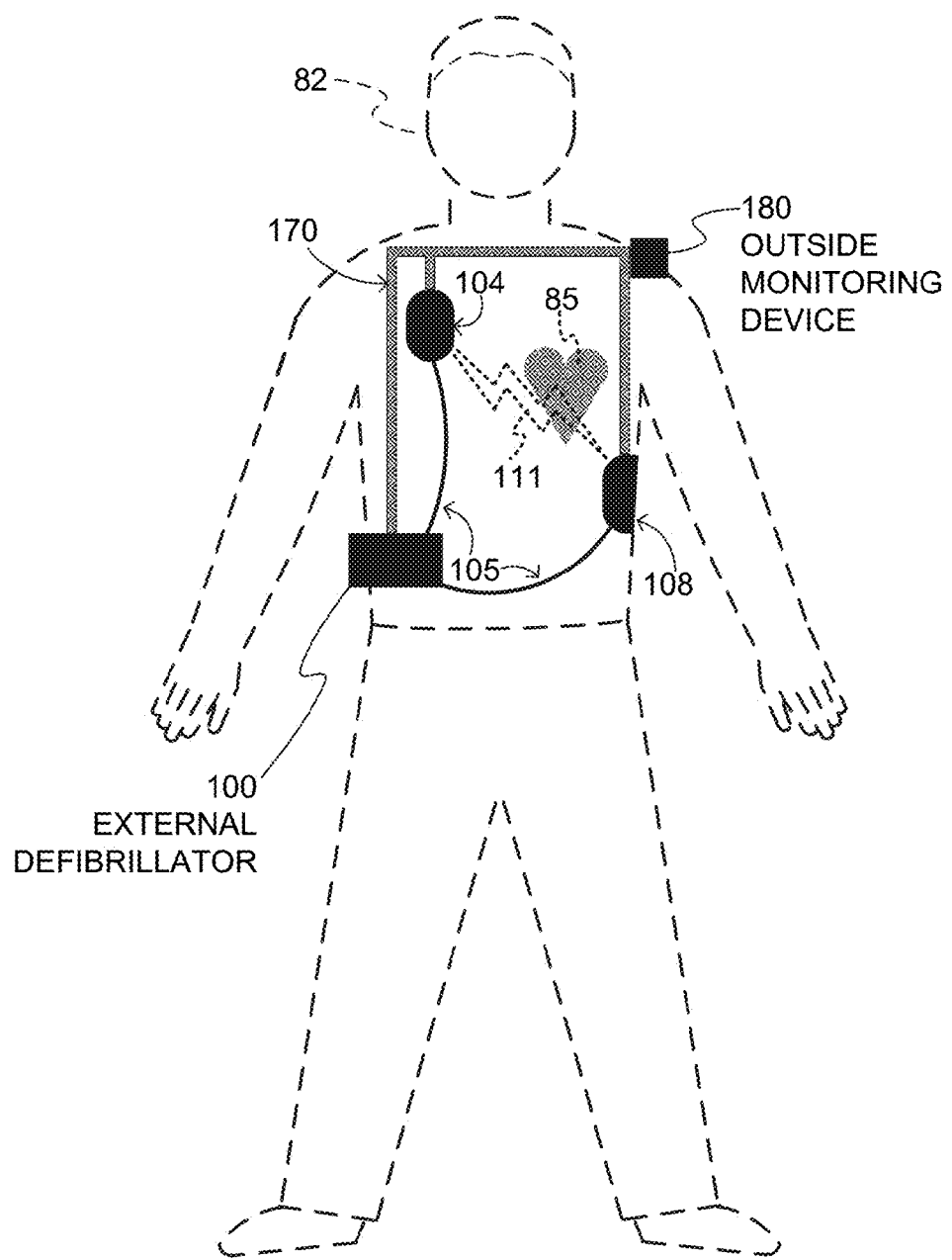
FIG. 1 is a diagram of components of a wearable defibrillator system, made according to embodiments.

FIG. 1 depicts components of a wearable defibrillator system made according to embodiments, as it might be worn by a person 82. A person such as person 82 may also be referred to as a patient and/or wearer, since that person wears components of the wearable defibrillator system.

In FIG. 1, a generic support structure 170 is shown relative to the body of person 82, and thus also relative to his or her heart 85. Structure 170 could be a harness, a vest, one or more belts, a garment, etc., as per the above. Structure 170 could be implemented in a single component, or multiple components, and so on. Structure 170 is wearable by person 82, but the manner of wearing it is not depicted, as structure 170 is depicted only generically in FIG. 1.

A wearable defibrillator system is configured to defibrillate the patient, by delivering electrical charge to the patient's body in the form of an electric shock. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock or electrical therapy shock, is intended to go through and restart heart 85, in an effort to save the life of person 82. Pulse 111 can also be one or more pacing pulses, and so on.

A prior art defibrillator typically decides whether to defibrillate or not based on an electrocardiogram ("ECG") of the patient. However, defibrillator 100 can defibrillate, or not defibrillate, also based on other inputs.

The wearable defibrillator system may optionally include an outside monitoring device 180. Device 180 is called an "outside" device because it is provided as a standalone device, for example not within the housing of defibrillator 100. Device 180 is configured to monitor at least one local parameter. A local parameter can be a parameter of patient 82, or a parameter of the wearable defibrillation system, or a parameter of the environment, as will be described later in this document.

Optionally, device 180 is physically coupled to support structure 170. In addition, device 180 can be communicatively coupled with other components, which are coupled to support structure 170. Such a component can be a communication module, as will be deemed applicable by a person skilled in the art in view of this disclosure.

Figure 2:
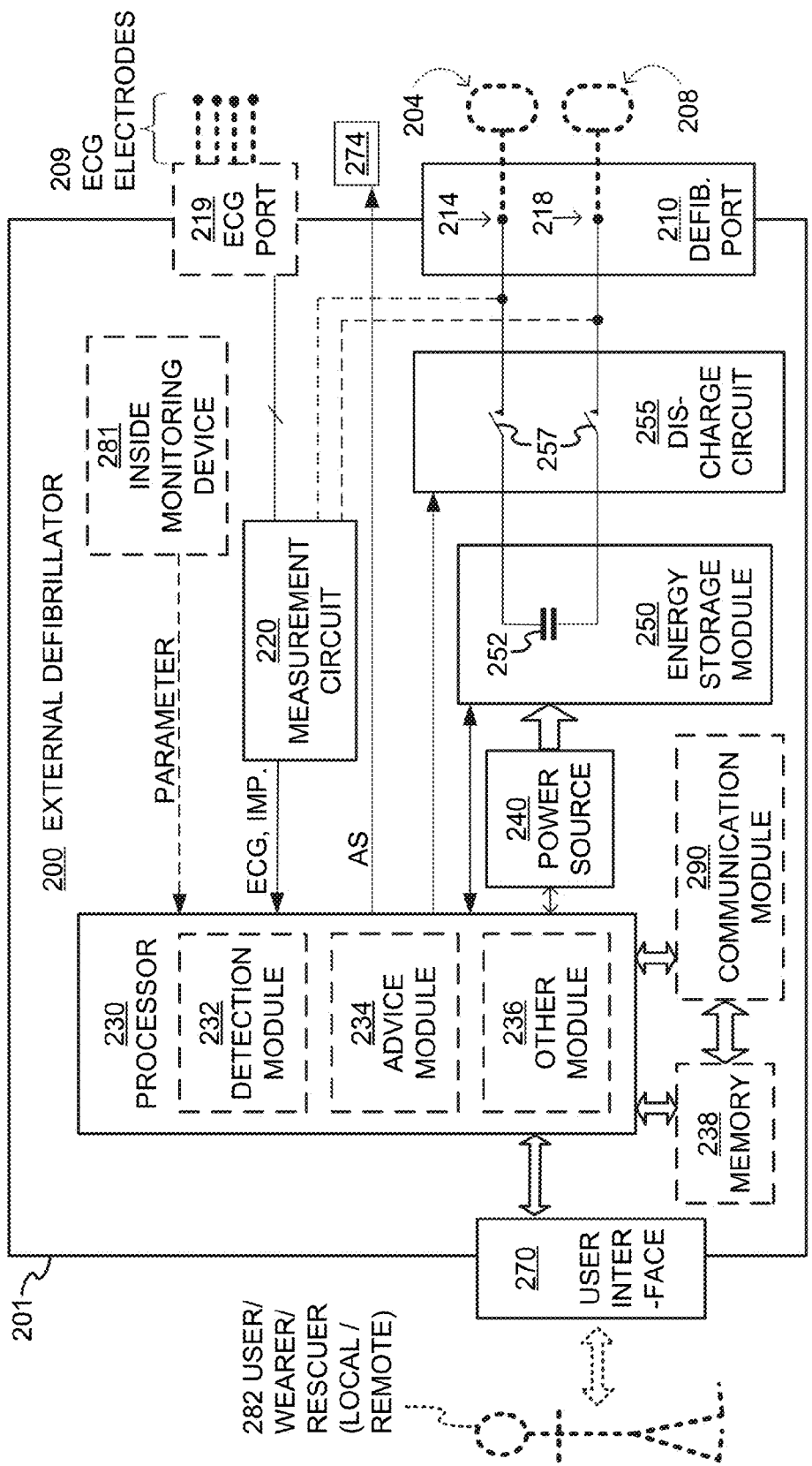
FIG. 2 is a diagram showing components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as person 82 of FIG. 1. Defibrillator 200 may further include a user interface 270 for a user 282. User 282 can be patient 82, also known as wearer 82, if conscious. Or user 282 can be a local rescuer at the scene, such as a bystander who might offer assistance, or a trained person. Or, user 282 might be a remotely located trained caregiver in communication with the wearable defibrillator system.

User interface 270 can be made in any number of ways. User interface 270 may include output devices, which can be visual, audible or tactile, for communicating to a user. User interface 270 may also include input devices for receiving inputs from users. For example, interface 270 may include a screen, to display what is detected and measured, provide visual feedback to rescuer 282 for their resuscitation attempts, and so on. Interface 270 may also include a speaker, to issue voice prompts, etc. Sounds, images, vibrations, and anything that can be perceived by user 282 can also be called human perceptible indications. Interface 270 may additionally include various controls, such as pushbuttons, keyboards, touchscreens, a microphone, and so on. In addition, discharge circuit 255 can be controlled by processor 230, or directly by user 282 via user interface 270, and so on.

Defibrillator 200 may include an internal monitoring device 281. Device 281 is called an "internal" device because it is incorporated within housing 201. Monitoring device 281 can monitor patient parameters, patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations.

Patient physiological parameters include, for example, those physiological parameters that can be of any help in detecting by the wearable defibrillation system whether the patient is in need of a shock, plus optionally their history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and maybe sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Monitoring device 180 or monitoring device 281 may include a motion detector, which can be made in many ways as is known in the art. Or, one of these monitoring devices could include a location sensor such as a Global Positioning System (GPS), which informs of the location, and the rate of change of location over time. Many motion detectors output a motion signal that is indicative of the motion of the detector, and thus of the patient's body. Patient state parameters can be very helpful in narrowing down the determination of whether SCA is indeed taking place.

System parameters of a wearable defibrillation system can include system identification, battery status, system date and time, reports of self-testing, records of data entered, records of episodes and intervention, and so on.

Environmental parameters can include ambient temperature and pressure. A humidity sensor may provide information as to whether it is raining. Presumed patient location could also be considered an environmental parameter. The patient location could be presumed if monitoring device 180 or 281 includes a GPS sensor.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged in defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on. Defibrillation electrodes 204, 208 can be made in a number of ways, such as by a thin piece of metal foil, such as tin or Ag/AgCl, etc.

Defibrillator 200 may optionally also have an ECG port 219 in housing 201, for plugging in ECG electrodes 209, which are also known as ECG leads. It is also possible that ECG electrodes 209 can be connected continuously to ECG port 219, instead. ECG electrodes 209 can help sense an ECG signal, e.g. a 12-lead signal, or a signal from a different number of leads, especially if they make good electrical contact with the body of the patient. ECG electrodes 209 can be attached to the inside of support structure 170 for making good electrical contact with the patient, similarly as defibrillation electrodes 204, 208.

Optionally and preferably, a wearable defibrillator system according to embodiments also includes a fluid that it can deploy automatically between the electrodes and the patient's skin. The fluid is preferably conductive, such as by including an electrolyte, for making a better electrical contact between the electrode and the patient's skin. Saline and a hydrogel are good examples. Electrically speaking, when the fluid is deployed, the electrical impedance between the electrode and the skin is reduced. Mechanically speaking, the fluid may have higher viscosity than water, such as by being a gel, so that it does not flow away, after it has been deployed. The fluid can be used for both defibrillation electrodes 204, 208, and ECG electrodes 209.

The fluid may be initially stored in a fluid reservoir, not shown in FIG. 2, which can be coupled to the support structure. In addition, a wearable defibrillator system according to embodiments further includes a fluid deploying mechanism 274. Fluid deploying mechanism 274 can be configured to cause at least some of the fluid to be released from the reservoir, and be deployed near one or both of the patient locations to which the electrodes are configured to be attached. In some embodiments, fluid deploying mechanism 274 is activated responsive to receiving activation signal AS from processor 230, prior to the electrical discharge.

Defibrillator 200 also includes a measurement circuit 220. Measurement circuit 220 receives physiological signals from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the patient's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or ECG electrodes 209 are not making good electrical contact with the patient's skin. These physiological signals can be sensed, and information about them can be rendered by circuit 220 as data, other signals, etc.

Defibrillator 200 also includes a processor 230. Processor 230 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can be considered to have a number of modules. One such module can be a detection module 232. Detection module 232 can include a ventricular fibrillation detector. Ventricular fibrillation is sometimes abbreviated as "VF". The patient's sensed ECG from measurement circuit 220 can be used by the VF detector to determine whether the patient is experiencing VF. Detecting VF is useful, because VF often results in SCA.

Another such module in processor 230 can be an advice module 234, which generates advice for what to do. The advice can be based on outputs of detection module 232. There can be many types of advice according to embodiments. As one example, a Shock Advisory Algorithm can render the advice to shock the patient by delivering a charge, as opposed to not shock the patient. Shocking can be for defibrillation, pacing, and so on.

Processor 230 can include additional modules, such as other module 236, for other functions. In addition, if monitoring device 281 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 238 is thus a non-transitory storage medium.

Memory 238, if provided, can include programs for processor 230, which processor 230 may be able to read, and execute. More particularly, the programs can include sets of instructions in the form of code, which processor 230 may be able to execute upon reading. Executing is performed by physical manipulations of physical quantities, and may result in the functions, processes, actions and/or methods to be performed, and/or the processor to cause other devices or components or blocks to perform such functions, processes, actions and/or methods. The programs can be operational for the inherent needs of processor 230, and can also include protocols and ways that decisions can be made by advice module 234. In addition, memory 238 can store prompts for user 282, if they are a local rescuer. Moreover, memory 238 can store data. The data can include patient data, system data and environmental data, for example as learned by monitoring device 281 and monitoring device 180. The data can be stored memory 238 before it is transmitted out of defibrillator 200, or stored there after it is received by it.

Defibrillator 200 may also include a power source 240. To enable portability of defibrillator 200, power source 240 typically includes a battery. Such a battery is typically implemented as a battery pack, which can be rechargeable or not. Sometimes, a combination is used, of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the wearable system. Module 250 is where some electrical energy is stored in the form of a charge, when preparing it for sudden discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of electrical charge, for delivering to the patient.

Defibrillator 200 moreover includes a discharge circuit 255. Circuit 255 can be controlled to permit the energy stored in module 250 to be discharged to nodes 214, 218, and thus also to defibrillation electrodes 204, 208. Circuit 255 can include one or more switches 257. Switches 257 can be made in a number of ways, such as by an H-bridge, and so on.

Defibrillator 200 can optionally include a communication module 290, for establishing one or more wired or wireless communication links with other devices of other entities, such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, episode information, electrical therapy attempted, CPR performance, system data, environmental data, and so on.

Defibrillator 200 can optionally include other components.

Figure 3:
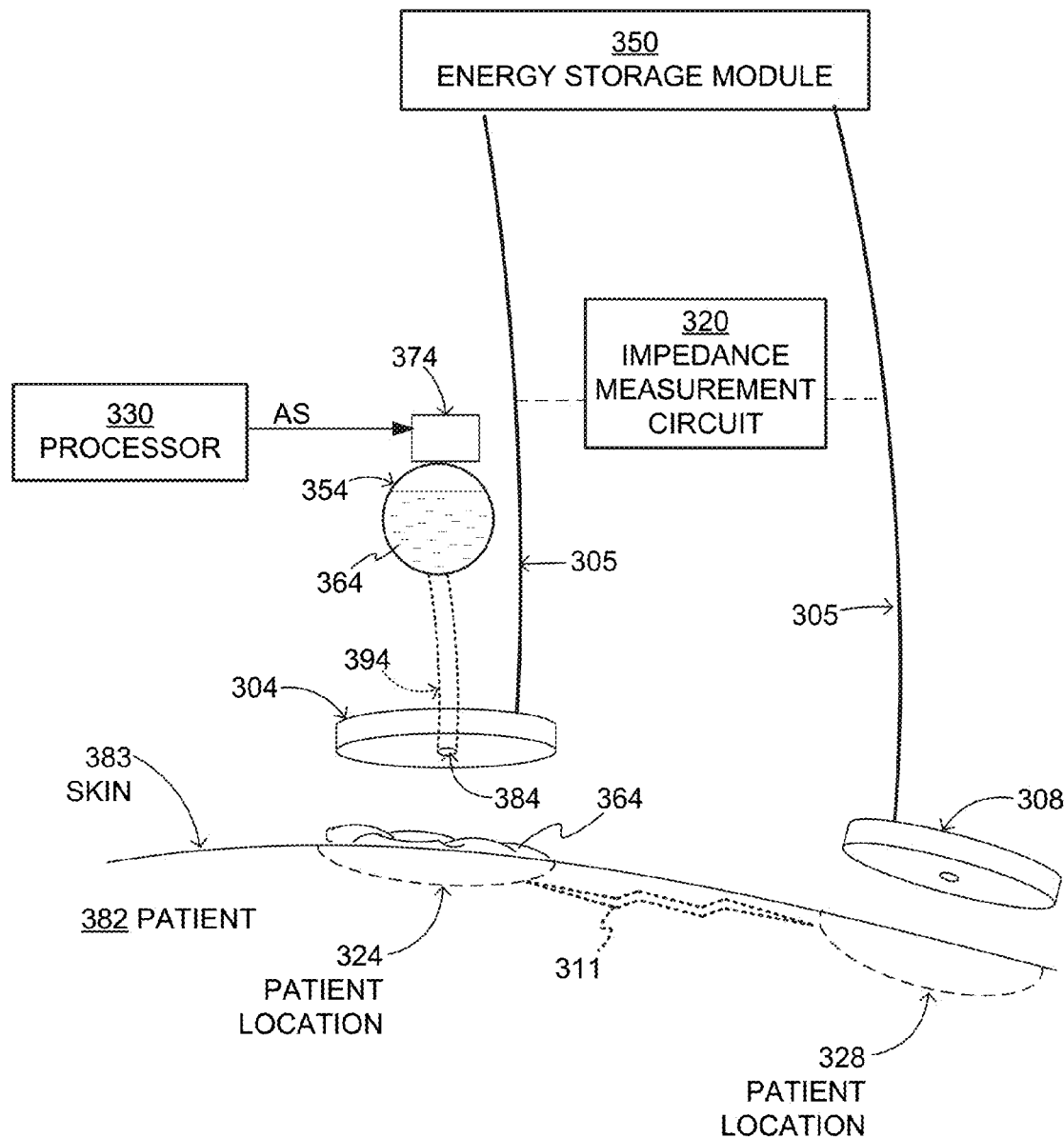
FIG. 3 is a diagram showing a set of components of a wearable defibrillator system made according to embodiments.

FIG. 3 is a diagram showing a set of components of a wearable defibrillator system made according to embodiments. A support structure can be provided, similarly to what was described above for support structure 170. A support structure is not shown in the set of FIG. 3, so as to not complicate the drawing. The support structure is intended to be worn by a patient 382.

An energy storage module 350, potentially similar to energy storage module 250, is configured to store an electrical charge. An electrode 304 has a lead 305, and another electrode 308 has another lead 305, similarly with similar items described above. Electrodes 304, 308 can be coupled with a support structure, such as support structure 170. By virtue of their placement on the support structure, and by how the support structure is to be worn by patient 382, electrodes 304, 308 can be configured to be applied at respective patient locations 324, 328 on skin 383 of the patient. Accordingly, the skin/electrode interface takes place at patient locations 324, 328. This way, electrodes 304, 308 are configured to deliver the charge stored in energy storage module 350 to patient locations 324, 328, when it is otherwise appropriate. Delivering the charge is also known as discharging, and a sample discharge 311 within the body of patient 382 is also shown.

It should be noted that electrodes 304, 308 can be configured to contact skin 383 directly, or be applied at respective patient locations 324, 328 over the patient's clothes. Either way, there is the challenge of minimizing, and hopefully removing, the hazard of a chemical or heat burn to skin 383 of patient 382. The challenge can be met by reducing the impedance at the skin/electrode interface, which may be accomplished by wetting with the appropriate fluid.

An impedance measurement circuit 320, potentially similar to impedance measurement circuit 220, can be configured to sense an impedance between two electrodes 304, 308. The sensed impedance is thus the one seen by the defibrillator via electrodes 304, 308. Once electrodes 304, 308 make good electrical contact with skin 383, the sensed impedance can be treated as the patient impedance. As will be seen below, releasing a fluid may decrease the impedance, in which case the sensed impedance can be the sensed decreased impedance.

The component set of FIG. 3 further includes a processor 330. Processor 330 can be similar to processor 230, and be configured to cause the charge stored in module 350 to be delivered, when appropriate.

Good electrical contact can be made according to embodiments by deploying a fluid with low impedance at patient locations 324, 328. More particularly, the set of FIG. 3 may also include a reservoir 354 that can be a single reservoir or system of reservoirs. Reservoir 354 can be configured to store a fluid 364, and can be coupled to the support structure. As such, reservoir 354 is preferably rugged or well insulated against external impact, and is preferably impermeable to liquid and gas, to minimize electrolyte contamination and/or dehydration during storage. In some embodiments it is flexible, like a pouch, and it can be a metalized plastic laminate pouch similar to that used in the packaging of medical products as well as food and beverage products. Packaging from metalized plastic laminate pouches are made from a low melting plastic interior layer (such as Low Density Polyethylene) and a thin layer of metal (e.g. aluminum, etc.). Other outer layers made from various plastics (e.g. polyester, Nylon, Mylar, Polypropylene, etc.) are also common for various purposes including labeling product with graphics. The advantages of an electrolyte reservoir constructed from metalized plastic laminate include being flexible, resisting impact pressures, size (thin), and limiting moisture vapor transmission. Being thin, reservoir 354 will not press as much against the patient's body. The reservoir can be the appropriate size, such as a capsule or larger.

Fluid 364 is the fluid that will be deployed at one or both of patient locations 324, 328. Fluid 364 can be an electrolyte, so as to conduct electricity well, and accordingly reduce the impedance sensed by impedance measurement circuit 320, when it is deployed.

The component set of FIG. 3 further includes a fluid deploying mechanism 374, similar to fluid deploying mechanism 274. Fluid deploying mechanism 374 may operate responsive to an activation signal AS from processor 330. When deploying mechanism 374 operates, it can be configured to cause at least some of fluid 364 to be released from reservoir 364. The fluid may be released all at once, or in doses. As will be seen, in some embodiments, it is released only as necessary, which may help preserve the ability to repeat as necessary later.

Upon being released, fluid 364 can be deployed near patient location 324. This can be accomplished in a number of ways. In some embodiments, reservoir 354 is located near electrode 304, and in fact can be attached to it. Release can be near electrode 304. A reservoir can include an exit mechanism that has a directing tube; the directing tube can be configured to deploy the released fluid towards the desired direction such as patient location 324.

Alternately, as shown in FIG. 3, release can be through an opening 384 in electrode 304. In other embodiments, a duct 394 is provided between reservoir 354 and opening 384, and fluid 364 also travels via duct 394 to patient location 324 for deployment. The inclusion of duct 394 in the system requires fluid 364 to travel longer for deployment, however.

Accordingly, when fluid 364 is so deployed, it can cause the sensed impedance to be decreased. In addition, optionally and preferably, a parallel mechanism is provided also for electrode 308, for deploying fluid also at patient location 328.

As a person skilled in the art will be able to discern, there can be any number of different designs for combinations of reservoirs, fluids, and fluid deploying mechanisms. Examples are now described.

In some embodiments, fluid deploying mechanism 374 simply builds pressure into reservoir 354, which causes fluid 364 to push its way out of reservoir 354 via an exit mechanism such as mentioned above. The exit mechanism can be merely a path of least resistance in the reservoir. Reservoir 354 could be a plastic capsule with a predefined area of least resistance, which can burst open when the pressure builds up. Or reservoir 354 could implement the exit mechanism by a valve that releases fluid 364, when the latter is above some threshold pressure. The pressure can build up when activation signal AS causes, for example, a burst, such as a small pyrotechnic explosion. Sample particular embodiments are now described.

Figure 4A:
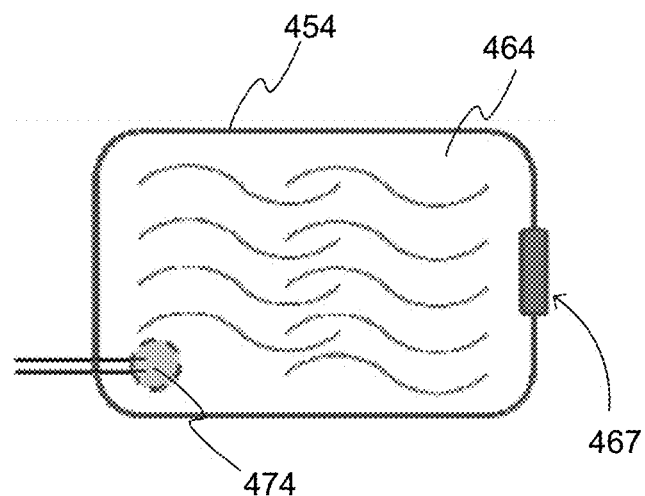
FIGS. 4A and 4B are diagrams of an embodiment of a reservoir, such as the reservoir of FIG. 3, before and after activation.
Figure 4B:
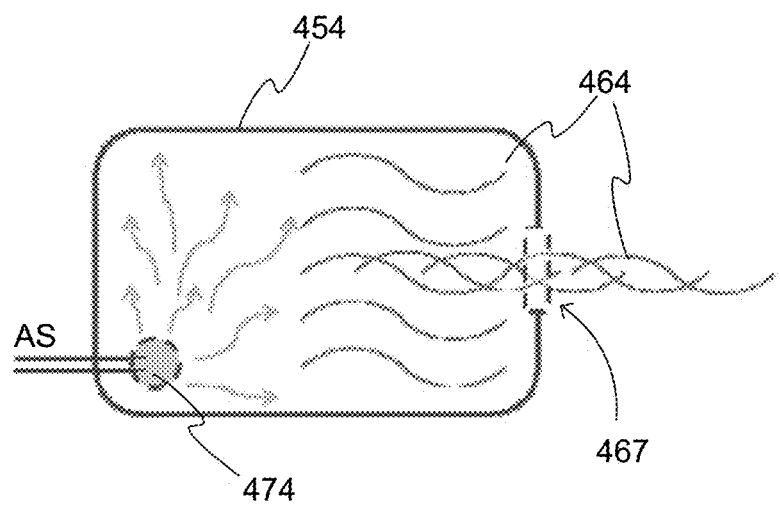

FIG. 4A shows a reservoir 454 that contains a fluid 464, has an exit mechanism 467, and is operable by a fluid deploying mechanism 474. In FIG. 4B, activation signal AS is received by fluid deploying mechanism 474. Gas can thus be directly generated within reservoir 454 by one or more gas generated propellants, such as nitrous oxide, carbon dioxide, etc. Accordingly, fluid 464 can be released from reservoir 454 via exit mechanism 467.

Figure 5A:
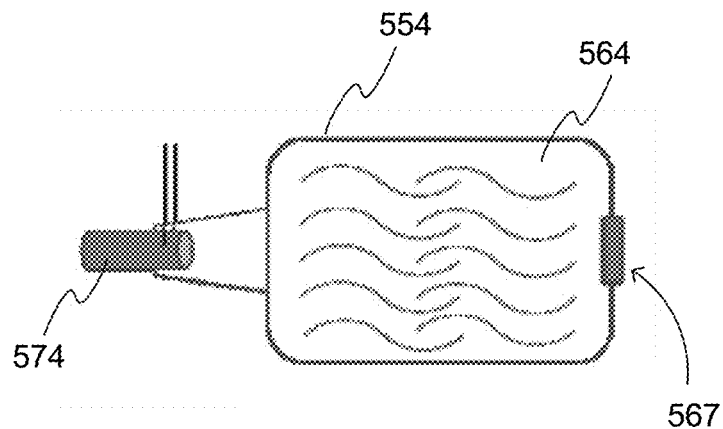
FIGS. 5A and 5B are diagrams of another embodiment of a reservoir such as the reservoir of FIG. 3, before and after activation.
Figure 5B:
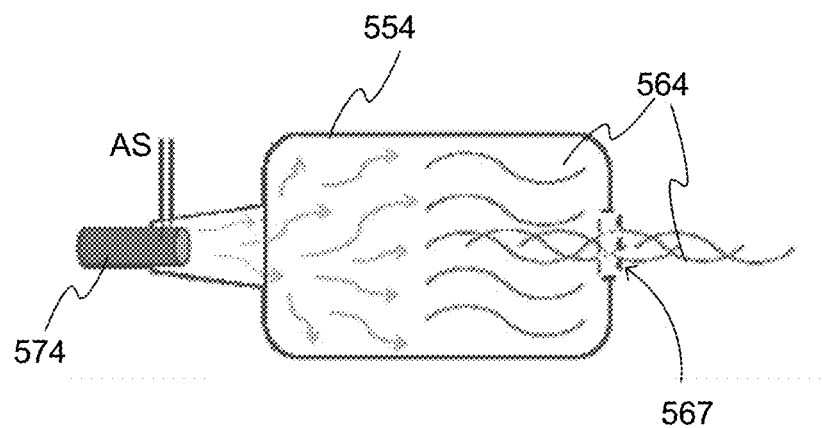

FIG. 5A shows a reservoir 554 that contains a fluid 564, has an exit mechanism 567, and is operable by a fluid deploying mechanism 574. In FIG. 5B, activation signal AS is received by fluid deploying mechanism 574. Remotely stored gas can thus be infused into reservoir 554 via a gas cartridge, such as a $CO_2$ canister, etc. Accordingly, fluid 564 can be released from reservoir 554 via exit mechanism 567.

Figure 6A:
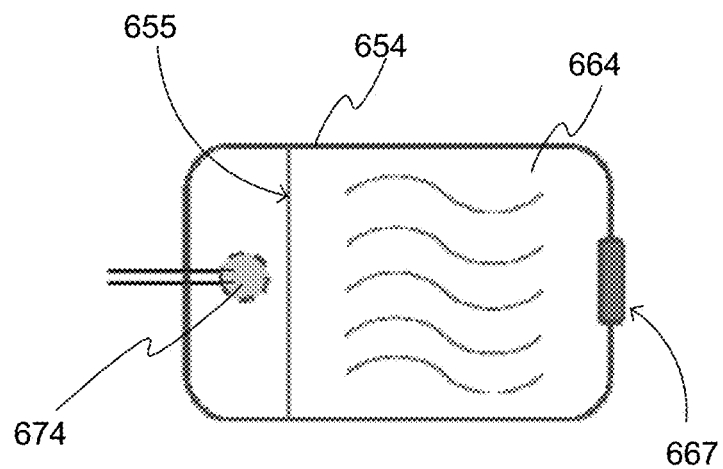
FIGS. 6A and 6B are diagrams of a different embodiment of a reservoir such as the reservoir of FIG. 3, before and after activation.
Figure 6B:
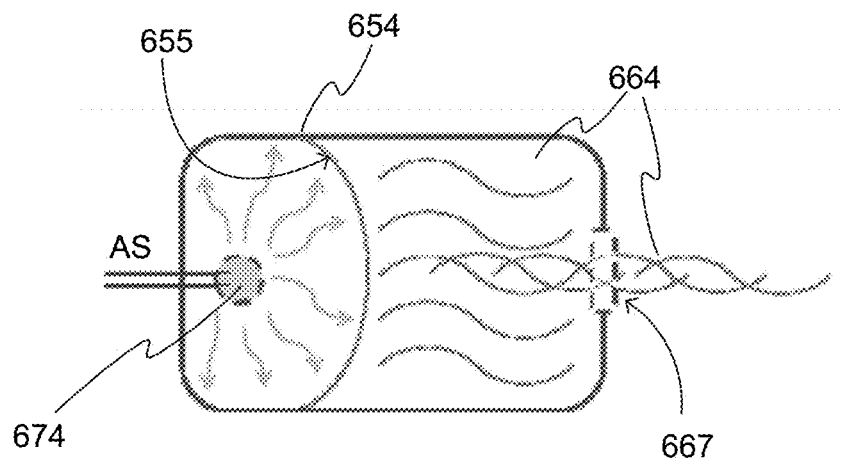

FIG. 6A shows a reservoir 654, which includes an elastic membrane 655 that defines two chambers. The right chamber has an exit mechanism 667. A fluid 664 is in the right chamber, and a fluid deploying mechanism 674 operates in the left chamber. In FIG. 6B, activation signal AS is received by fluid deploying mechanism 674. Gas or vapor can be generated inside the left chamber, and an elastic membrane 655 can push into the right chamber. Methods of gas generation include gas generated propellants (e.g. nitrous oxide, carbon dioxide, etc.), a gas cartridge (e.g. $CO_2$ canister), a substance such as water undergoing a phase change (e.g. liquid-to-gas, etc.), and so on. Accordingly, fluid 664 can be released from reservoir 654 via exit mechanism 667.

In some embodiments, the fluid deploying mechanism controls the release of the fluid more strictly. An example of such a controlled release mechanism is when the fluid deploying mechanism includes a pump, which is configured to pump the fluid out of the reservoir. The pump generates the pressure required. In such embodiments, deploying the fluid includes pumping. An example is now described.

FIG. 7 shows an embodiment where a reservoir 754 contains a fluid 764. An electrode 704, which can be similar to electrode 304, has an opening 784. A pump 777 may pump fluid 764 from reservoir 754 via duct 794 to opening 784. Duct 794 may include the appropriate tubing, and measures should be taken to prevent duct 794 from being crimped. Various positive displacement pumps with self-priming functionality are suitable for this application. Pump options include a peristaltic pump, a gear pump, a rotary screw, and a diaphragm pump, to name a few. A MEMS programmable pump or a piezoelectric pump is also applicable. The main purpose of pump 777 is to automatically pump the desired amount of fluid 764 to the patient location when needed. Pumping can be controlled electronically, or triggered, by the processor.

Returning to FIG. 3, in other embodiments, reservoir 354 may simply open near opening 384, and fluid 364 leaks out. In such embodiments, it is preferable to use an embodiment of an electrode that includes a fluid retention structure. An example is now described.

FIG. 8 is a diagram of an electrode 810 made according to embodiments. Electrode 810 may be part of a wearable defibrillator according to embodiments, or a part of a monitor-defibrillator or part of an Automated External Defibrillator (AED).

Electrode 810 includes a conductive pad 822, and a lead 805 similar to lead 305. Conductive pad 822 can include a thin piece of metal foil, such as tin or Ag/AgCl. Other conductors may also be suitable, as would be apparent to one skilled in the art. A woven conductive carbon sheet is also applicable.

Conductive pad 822 optionally includes an opening 884, through which fluid may be released. The fluid may be released locally, or be guided by a duct 894, as per the above.

Electrode 810 further includes a fluid retention structure 824 made according to embodiments. Fluid retention structure 824 may be coupled, or attached to conductive pad 822. By its placement relative to other components, fluid retention structure 824 can be configured to be placed near the patient location of electrode 810. Accordingly, if fluid is leaked to fluid retention structure 824, the latter may substantially retain it. And the fluid retention structure 824 may be at the patient location, thus keeping the fluid there. In addition, due to its constitution, fluid retention structure 824 may distribute the fluid substantially evenly around the patient location. As such, the fluid may be caused to be released from the reservoir and be deployed into fluid retention structure 824.

Fluid retention structure 824 may be implemented in different ways. It can be thin, flexible, and comfortable against the patient's skin. For example, it can be made from any hydrophilic substance that has a characteristic to absorb and/or adsorb the delivered electrolyte to lower the impedance of the electrode. It may include a sponge such as an open-cell sponge, and/or a piece of cellulose. Cellulose, like cotton fabric, also works in embodiments. By absorbing/adsorbing the low viscosity electrolyte fluid, fluid retention structure 824 would prevent at least some of the fluid from leaking away from the patient location. To remain at its intended location, fluid retention structure 824 can even be attached to the support structure. Sewing is a suitable method to integrate the fluid retention structure to a support structure that is implemented as a garment.

Another suitable method to attach fluid retention structure 824 to the support structure would be to melt the substrates together, for example by means of ultrasonic welding or similar application. There may be a benefit for fluid retention structure 824 to be disposable and/or replaceable, and therefore a method to connect or attach fluid retention structure 824 to the support structure would be advantageous. One potential solution includes creating a dedicated pocket for sliding fluid retention structure 824 into. Another potential solution would be to attach fluid retention structure 824 to the support structure by means of Velcro, snaps or other method.

The released fluid may soak the fluid retention structure by a capillary effect and/or a wicking effect. Such effects may decrease the time required to saturate the electrode system, and be ready for discharge faster. High saturation speed can be facilitated by the use of a fabric constructed from fibers (natural or synthetic, woven or nonwoven) that aid in distributing (wicking) the fluid throughout fluid retention structure 824. Moreover, a component may be included for keeping the individual electrodes hermetically or electrically separated, so as to avoid current shunting between the electrodes.

Further, a combination of pad and fluid retention structure can be implemented with a structure made by a fabric that includes thin conductive wires woven into the fabric. Conductors with a low impedance (e.g. <1 ohm per square inch) may be used.

An advantage is that, for such releasing, the fluid need not be ejected forcefully from the reservoir but only leaked. Additionally, the fluid need not be high viscosity. In fact, it will deploy more easily with a lower viscosity. Further, the defibrillation electrodes need not make contact, or at least full contact, with the patient's skin for the long term. The person's ECG may be monitored by smaller, ECG electrodes. Moreover, the need to defibrillate the person, or to generate the suspicion that the person may need defibrillation, may be derived otherwise.

One more set of sample embodiments is now provided, for a reservoir and a fluid deploying mechanism. It will be appreciated that these embodiments can be used to implement either fluid being ejected from the reservoir or merely leaking, such as to electrode 810.

Figure 9A:
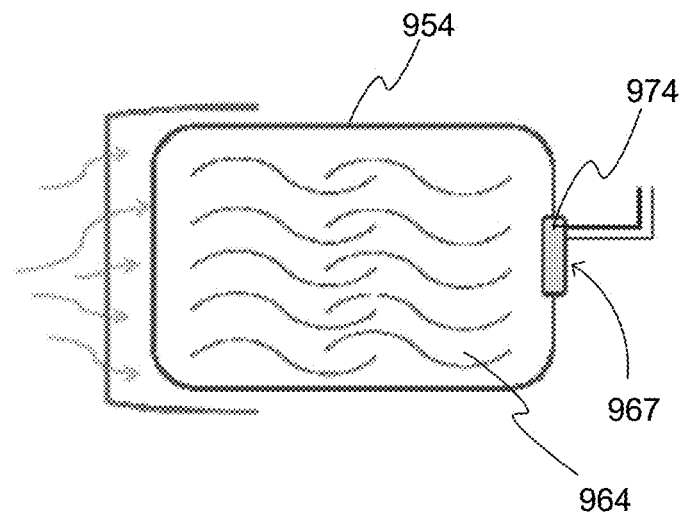
FIGS. 9A and 9B are diagrams of one more embodiment of a reservoir such as the reservoir of FIG. 3, before and after activation.
Figure 9B:
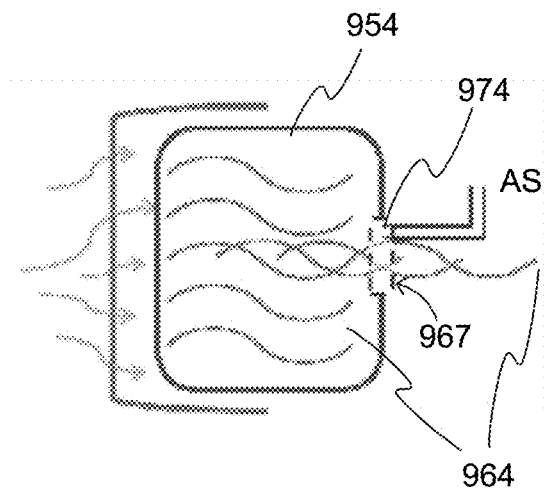

FIG. 9A shows a reservoir 954 that contains a fluid 964, has an exit mechanism 967, and is operable by a fluid deploying mechanism 974. A release feature is integrated into the walls of reservoir 954. In FIG. 9B, activation signal AS is received by fluid deploying mechanism 974. Once activated, and potentially maintained by activation signal AS, the release feature will produce an orifice for liquid transfer. External pressure provided by the support structure and/or walls of reservoir 954 will assist in channeling the fluid 964 out of reservoir 954. Potential release feature mechanisms include a) an electric valve (e.g. MEMS device, piezoelectric ceramic, solenoid valve, etc.), b) a mechanical deformation mechanism (e.g. pierced actuation, reservoir being an inflated balloon, etc.), c) melted substrate (e.g. reservoir housing wall, plastic film, plastic/wax/low-melting alloy plug). A resistive Nichrome wire could be utilized to supply the localized (focused) heat required for melting the substrate. Accordingly, fluid 964 can be released from reservoir 954 via exit mechanism 967.

Returning to FIG. 3, the stored charge can be delivered to patient locations 324, 328 depending on whether the impedance sensed by impedance measurement circuit 320 meets a discharge condition. Accordingly, processor 330 can be configured to cause the stored charge to be delivered, when the discharge condition is met. This coordination can be relevant given that the sensed impedance may be reduced because of releasing fluid 364. Examples are now described.

Figure 10:
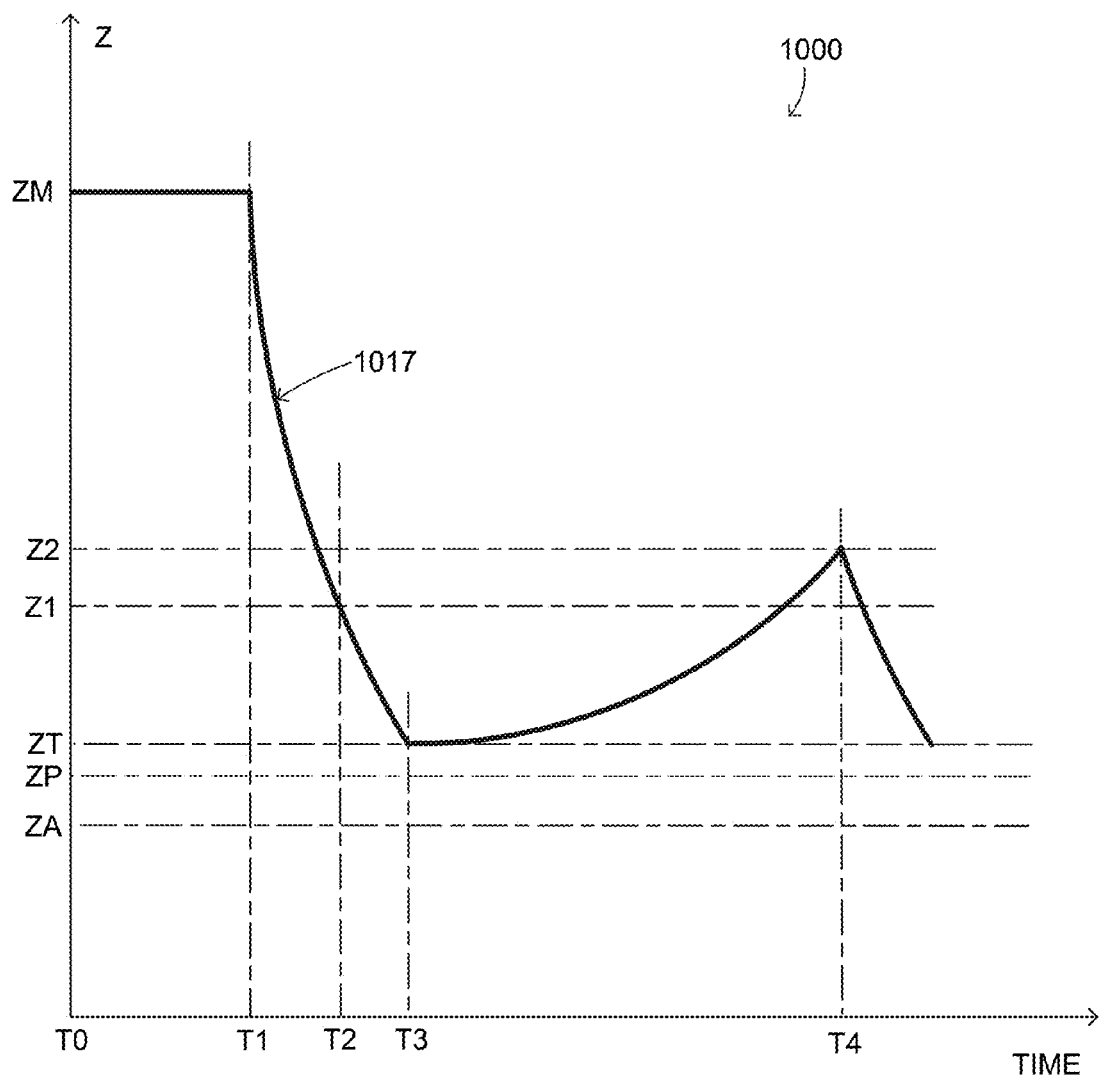
FIG. 10 is a time diagram of an impedance sensed according to embodiments by a system having components such as the components of FIG. 3.

FIG. 10 is a time diagram 1000 of an impedance sensed according to embodiments by a system having components such as the components of FIG. 3. The horizontal axis indicates time. The vertical axis indicates the sensed impedance Z, not to scale. The impedance may be sensed multiple times, and its changing values can be tracked.

The sensed impedance Z could follow time profile 1017. At time T0, i.e. before anything happens, Z could have a value of ZM. The value of ZM could be infinity for an open circuit, or a very large value if the electrodes were somehow contacting the patient, but not making good electrical contact.

At time T1, the fluid starts being released. It can be all the fluid, or at least some of the fluid but not all. The reason for releasing the fluid could be that a determination has been made that the charge needs to be delivered, or merely that a more reliable ECG needs to be taken on suspicion that the charge may need to be delivered.

As the fluid is released, the sensed impedance starts to decrease. Optionally, an ECG measurement can be taken via the electrodes, taking advantage of the reduced impedance.

As the sensed impedance continues to decrease, immediately after time T2, the sensed impedance has a value below a first threshold Z1. In some embodiments, the discharge condition is that the sensed impedance has a value below a first threshold. Accordingly, the charge is delivered with the confidence that the impedance is low enough. If the charge delivery depends on the instantaneous value of the impedance, the rate of decrease of the sensed impedance may also optionally be taken into effect for forecasting more exactly the impedance at the time of actual discharge. The rate of change can include linear and non-lineal components.

The first threshold can be set in a number of ways. For example, it can be a fixed value, such as 500 Ohm. Or it can depend on the intended therapy. For example, a determination can be made by the processor that the charge needs to be delivered, for a first electrical therapy or a second electrical therapy. The first electrical therapy could be defibrillation, and the second electrical therapy could be pacing, such as anti-bradycardia pacing. The first threshold Z1 can have a first value if the needed delivery of the charge is appropriate for the first electrical therapy, and a second value if the needed delivery of the charge is appropriate for the second electrical therapy.

The values of thresholds, such as the first threshold, can be set in a number of ways. For example, the first threshold Z1 can be a fixed value, such as 500 Ohm.

At time T3, the sensed impedance may settle at a terminal value ZT. Preferably T3 is not very long after T1, and preferably less than a minute. The value ZT would be the sum of the actual patient impedance ZP, plus a difference made from the quality of the contact of the electrode and the patient, as assisted by the deployment of the fluid. In other words, the difference between ZT and ZP is what is accomplished by the released fluid. For defibrillation, it is desirable to have this difference low (e.g. <3 ohms). For external pacing, it is desirable for the difference to be higher (e.g. ~500 ohms). Higher impedance pacing electrodes distribute the current causing less pain.

In some embodiments, the intent may be to wait until the value settles to the terminal value ZT, for optimum use of the impedance. Of course, whether the value is settling can be established with a number of different criteria. For example, the discharge condition can be that the sensed impedance has a value that changes less than a threshold in a given amount of time. And that threshold could be defined as a percentage of the instantaneous sensed value.

In some embodiments, the discharge condition is that a timeout threshold has elapsed since, causing at least some of the fluid to be released. These embodiments can accommodate the possibility that the fluid may be all spent, or the fluid deployment mechanism has been damaged, and so on.

Whether the charge is delivered or not, after some time, the sensed impedance may start deteriorating, which means increasing again. This could be for a number of reasons, such as the fluid evaporating, drying off, or leaking away from the patient locations. For example, at time T4, the sensed impedance Z2 may have reached a second threshold Z2. Optionally Z2 could have the same value as Z1, but that is not required. In some embodiments, the fluid releasing mechanism can be caused to release some more of the fluid, if the impedance is sensed to be above second threshold Z2.

It is also possible that the electrodes are not well connected. In that case, the discharge condition can again be that a timeout threshold has elapsed.

It is further possible that the fluid has leaked a lot, and in fact has established a conductive bridge outside the patient body. In that case, the sensed impedance can become much less than the minimum possible impedance ZP. Accordingly, in some embodiments, a user interface such as user interface 270 can be configured to output an alert, if the sensed impedance decreases below an alert threshold ZA. In the case of wearable defibrillators, patient impedance ZP may have been known in advance rather accurately by the doctor fitting the patient, and alert threshold ZA can be set as a fraction of ZP, for example 70% of ZP.

In some embodiments, a time profile of the sensed impedance, such as time profile 1017, is stored in a memory such as memory 238. Then it can be exported along with other patient data and event data, analyzed and reviewed.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 11:
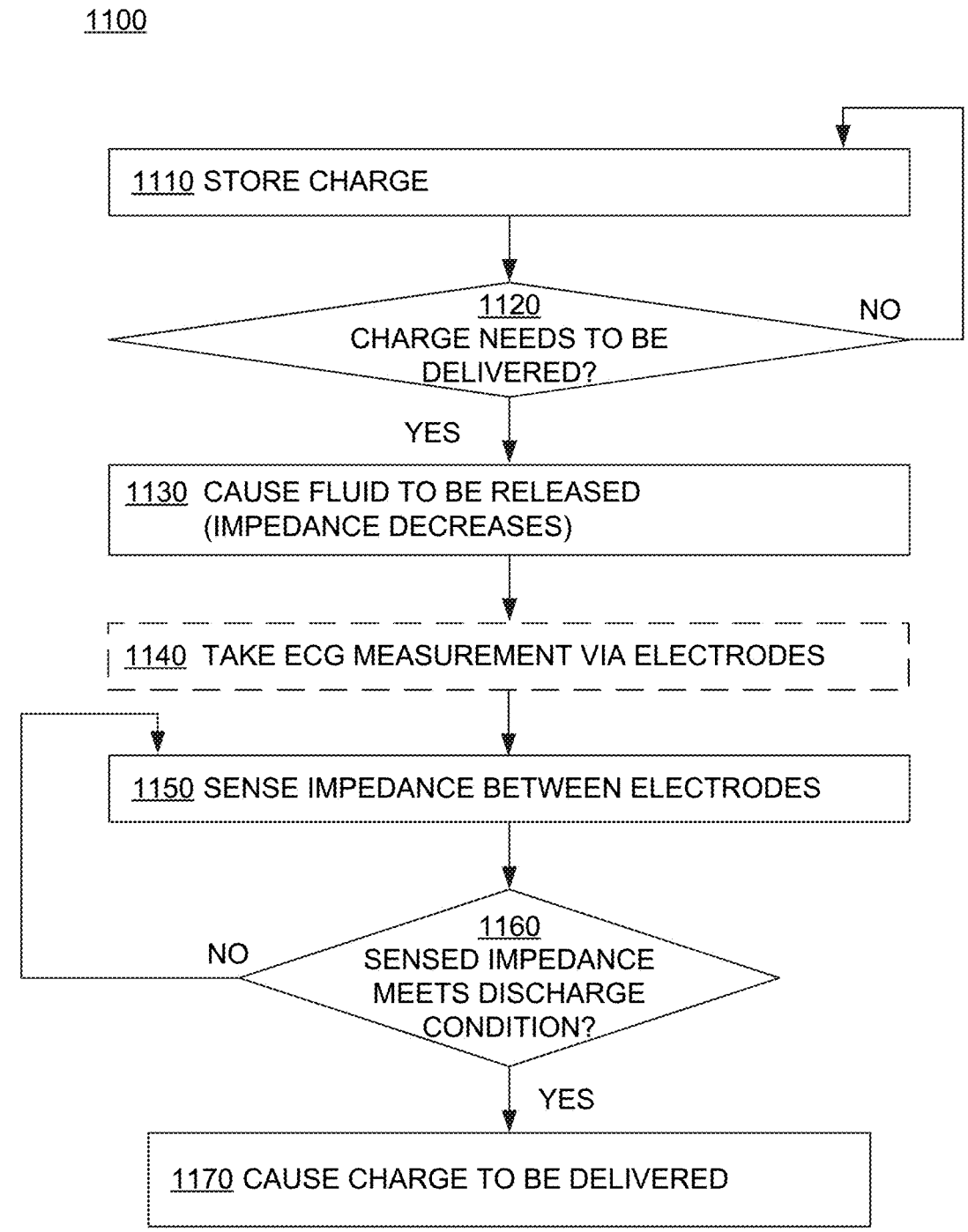
FIG. 11 is a flowchart illustrating methods according to embodiments.

FIG. 11 shows a flowchart 1100 for describing methods according to embodiments. The methods of flowchart 1100 may also be practiced by embodiments of defibrillator systems described above, and the individual operations of flowchart 1100 may be augmented by, and find explanation in the above descriptions.

According to an operation 1110, a charge is stored. According to another, optional operation 1120, a determination is made as to whether the charge needs to be delivered. If not, the process may return to operation 1110.

According to another operation 1130, fluid is caused to be released from a reservoir, and be deployed near at least one of two intended patient locations. The fluid may cause the impedance to be decreased.

According to another, optional operation 1140, an ECG measurement is taken via electrodes. According to another operation 1150, an impedance is sensed between the electrodes. The impedance may be changing, as was explained with reference to FIG. 10. For example, the impedance could be decreasing, due to the fluid being released at operation 1130.

According to another operation 1160, it is determined whether a discharge condition is met. The discharge condition can be as above. If not, then execution may return to operation 1150, or another operation.

If at operation 1160 it is determined that the discharge condition is met, then according to another, optional operation 1170, the charge is caused to be delivered to the patient locations via the electrodes. The charge delivery may be according to an intended electrical therapy, and so on.

Additional operations are also possible. For example, an alert may be output, if the sensed impedance decreases below an alert threshold. Plus, a time profile of the sensed impedance is stored in a memory, and so on.

Figure 12:
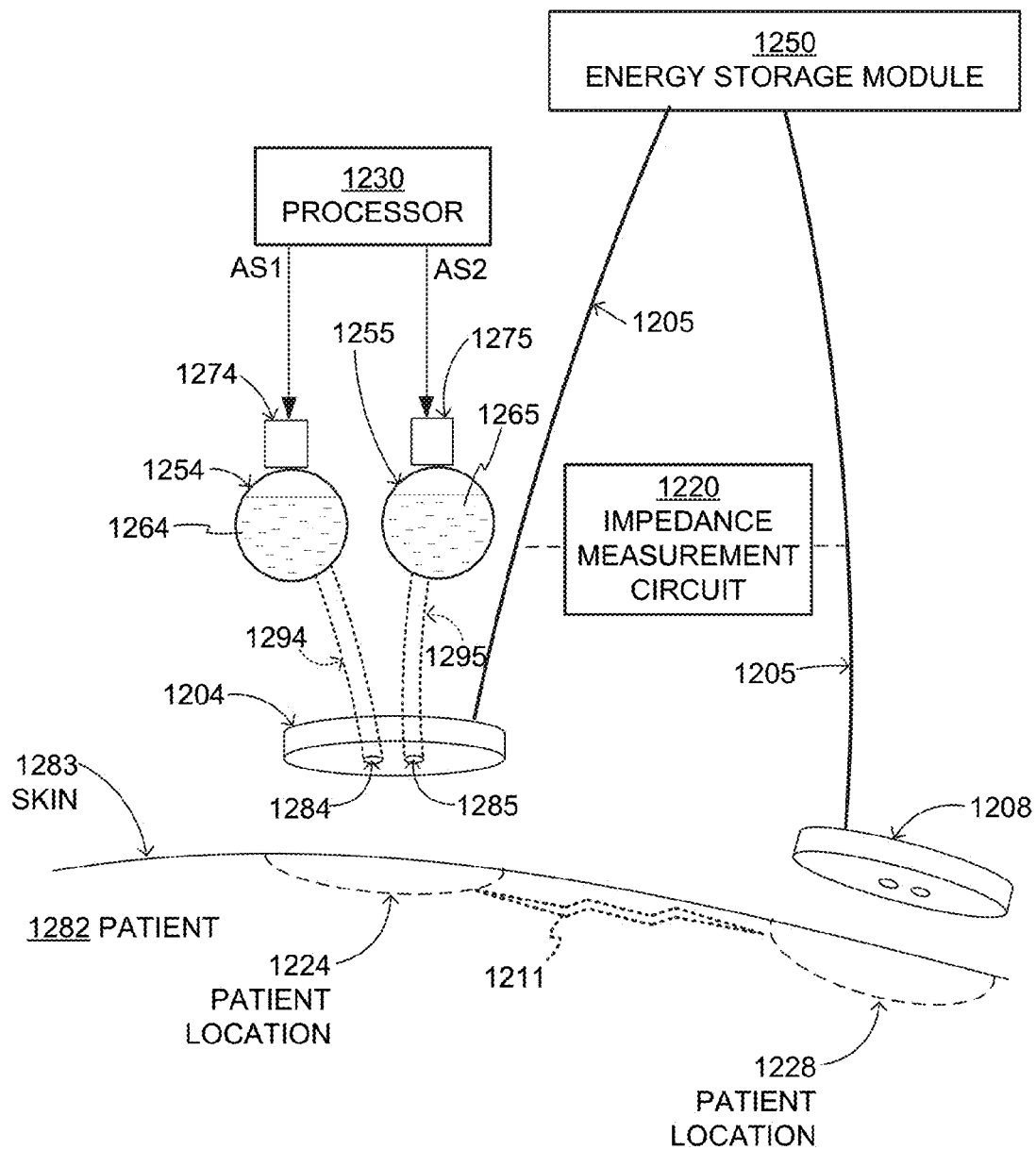
FIG. 12 is a diagram showing a set of components of a wearable defibrillator system made according to embodiments.

FIG. 12 is a diagram showing a set of components of a wearable defibrillator system made according to embodiments. A support structure can be provided, similarly to what was described above for support structure 170. A support structure is not shown in the set of FIG. 12, so as to not complicate the drawing. The support structure is intended to be worn by a patient 1282.

An energy storage module 1250, potentially similar to energy storage module 250, is configured to store an electrical charge. An electrode 1204 has a lead 1205, and another electrode 1208 has another lead 1205, similarly with similar items described above. Electrodes 1204, 1208 can be coupled with the support structure. By virtue of their placement on the support structure, and by how the support structure is to be worn by patient 1282, electrodes 1204, 1208 can be configured to be applied at respective patient locations 1224, 1228 on skin 1283 of patient 1282. This way, electrodes 1204, 1208 are configured to deliver the charge stored in energy storage module 1250 to patient locations 1224, 1228, when it is otherwise appropriate. A sample discharge 1211 is also shown. It should be noted that electrodes 1204, 1208 can be configured to contact skin 1283 directly, or be applied at respective patient locations 1224, 1228 over the patient's clothes.

An impedance measurement circuit 1220, potentially similar to impedance measurement circuit 220, can be configured to sense an impedance between two electrodes 1204, 1208. The sensed impedance is thus the one seen by the defibrillator via electrodes 1204, 1208.

The component set of FIG. 12 further includes a processor 1230. Processor 1230 can be similar to processor 230, and be configured to make a determination as to whether the patient needs one of a first electrical therapy and a second electrical therapy, such as defibrillation or pacing as described above. Processor 1230 can be further configured to cause the charge stored in module 1250 to be delivered, when appropriate, for administering the needed first or second electrical therapy.

The component set of FIG. 12 can further make good electrical contact by distributing fluids, either cumulatively or alternatively. More particularly, the set of FIG. 12 may also include reservoirs 1254, 1255, which can be coupled to the support structure. Reservoirs 1254, 1255 can be configured to store respective fluids 1264, 1265, which can be as described above. Fluids 1264, 1265 can be similar to each other, or different. Fluids 1264, 1265 can be configured to be deployed at one or both of patient locations 1224, 1228.

The component set of FIG. 12 further includes fluid deploying mechanisms 1274, 1275, similar to fluid deploying mechanism 274. Fluid deploying mechanisms 1274, 1275 may operate responsive to respective activation signals AS1, AS2 from processor 1230. When deploying mechanism 1274 operates, it can be configured to cause at least some of fluid 1264 to be released from reservoir 1254. Similarly, when deploying mechanism 1275 operates, it can be configured to cause at least some of fluid 1265 to be released from reservoir 1255.

Upon being released, fluids 1264, 1265 can be deployed near patient location 1224. This can be accomplished in a number of ways. In some embodiments, both reservoirs 1254, 1255 are located near electrode 1204, and in fact can be attached to it. Release of first fluid 1264 can be near electrode 1204, or through an opening 1284 through electrode 1204. In other embodiments, a duct 1294 is provided between reservoir 1254 and opening 1284. Additionally, release of second fluid 1265 can be near electrode 1204, or through an opening 1285 through electrode 1204. In other embodiments, a duct 1295 is provided between reservoir 1255 and opening 1285. In some embodiments, openings 1284 and 1285 are merged.

In some embodiments, fluids 1264, 1265 are deployed depending on the needed electrical therapy that will be administered by the discharge. So, first fluid deploying mechanism 1274 can be configured to cause at least some of first fluid 1264 to be released from first reservoir 1254 and be deployed near at least one of patient locations 1224, 1228, if the determination is that the first electrical therapy is needed. For example, if the first electrical therapy is defibrillation, first fluid 1264 can be a saline solution with a relatively high salt content (e.g. 0.9% NaCl) to provide a low impedance.

Similarly, second fluid deploying mechanism 1275 can be configured to cause at least some of second fluid 1265 to be released from second reservoir 1255 and be deployed near at least one of patient locations 1224, 1228, if the determination is that the second electrical therapy is needed. For example, if the second electrical therapy is pacing, second fluid 1265 can be an electrolyte with much less salt than 0.9% NaCl, creating an electrode with a relatively higher impedance.

All the previously mentioned possibilities optionally also apply also to the embodiments of FIG. 12. For example, one of more of electrodes 1204, 1208 may have an attached fluid retention structure, the stored charge may be delivered after a sensed impedance meets a discharge condition, and so on.

Moreover, a sensor can be provided used to monitor the level (amount) of fluid present within the reservoir. The level can be checked during self-test. As the level drops below the defined threshold, a notification can be provided to the attending physician, a message can be sent to service for replacement, etc. Further, a reservoir impedance check and/or a date code check can further be performed, to ensure the electrolyte is viable. The reservoir can be packaged and/or sold separately, or with the electrodes for replacement when used or expired.

Figure 13:
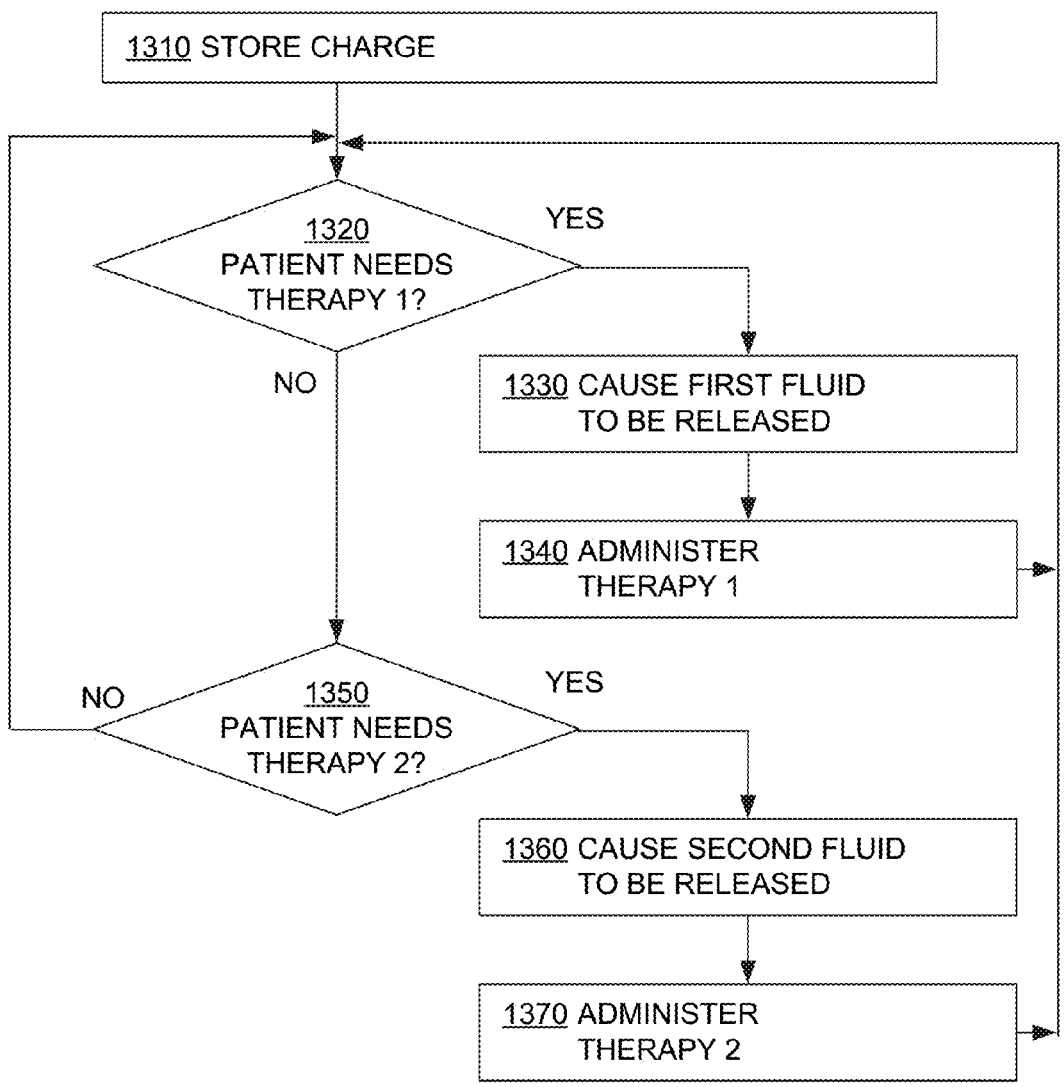
FIG. 13 is a flowchart illustrating methods according to embodiments.

FIG. 13 shows a flowchart 1300 for describing methods according to embodiments. The methods of flowchart 1300 may also be practiced by embodiments defibrillator systems described above. In addition, and the individual operations of flowchart 1300 may be augmented by, and find explanation in the above descriptions.

According to an operation 1310, charge is stored.

Then a determination may be made as to whether the patient needs one a first electrical therapy or a second electrical therapy, either one of which may be administered by discharge. So, in some embodiments, according to another operation 1320, it is determined whether the patient needs a first therapy; if not, then according to another operation 1350, it is determined whether the patient needs a second therapy. Again, if not, execution can loop to the same two operations.

If at operation 1320 the first therapy is needed then, according to another operation 1330, the first fluid is caused to be released from a first reservoir and be deployed near a patient location. Then, according to another operation 1340, the first therapy is administered, and execution may return to operation 1320.

If at operation 1350 the second therapy is needed then, according to another operation 1360, the second fluid is caused to be released from a second reservoir and be deployed near a patient location that could be the same as the location of operation 1330. Then, according to another operation 1370, the second therapy is administered, and execution may return to operation 1320.

In either case, the charge can be caused to be delivered via the electrodes for administering the needed one of the available electrical therapies.

Additional operations are also possible. For example, an impedance between the two electrodes may be sensed, and the stored charge can be delivered after the sensed impedance meets a discharge condition. Additionally, an alert may be output, if the sensed impedance decreases below an alert threshold. Plus, a time profile of the sensed impedance is stored in a memory, and so on.

Figure 14:
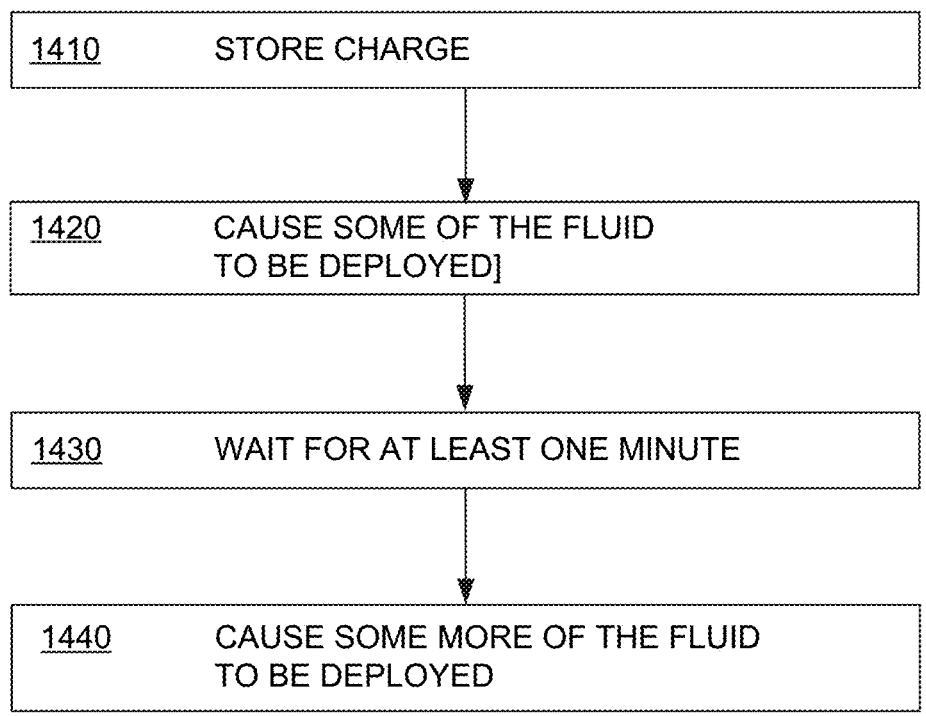
FIG. 14 is a flowchart illustrating methods according to embodiments.

FIG. 14 shows a flowchart 1400 for describing additional methods according to embodiments. The methods of flowchart 1400 may also be practiced by embodiments described above, including by embodiments of FIG. 3 and FIG. 12. In addition, the individual operations of flowchart 1400 may be augmented by, and find explanation in the above descriptions.

According to an operation 1410, a charge is stored.

According to another operation 1420, at least some of the fluid is caused to be released from the one or more reservoirs and be deployed near a certain one of the patient locations. The fluid can be all the same, or different in different reservoirs.

According to another operation 1430, execution waits for at least one minute before deploying any more, during which time an ECG may be taken, some of the electrical charge may be delivered, and so on. The patient may be deemed well for some time, but then not anymore, and so on.

According to another operation 1440, at least some more of the fluid is caused to be released from the one or more reservoirs, and be deployed near the certain patient location.

Operation 1440 may be repeated after more pauses, and so on. Such is particularly useful if a patient will need multiple electrical discharges in a single episode, as may happen in a number of scenarios. Sometimes episodes are prolonged. Defibrillation may need to be repeated. Anti-bradycardia pacing may need to last an hour or more, before help arrives. Embodiments, by being able to replenish the fluid, may sustain the patient better.

Additional operations are also possible. For example, an impedance between the two electrodes may be sensed, and the stored charge can be delivered after the sensed impedance meets a discharge condition. Additionally, an alert may be output, if the sensed impedance decreases below an alert threshold. Plus, a time profile of the sensed impedance is stored in a memory, and so on.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

This description includes one or more examples, but that does not limit how the invention may be practiced. Indeed, examples or embodiments of the invention may be practiced according to what is described, or yet differently, and also in conjunction with other present or future technologies.

Reference to any prior art in this specification is not, and should not be taken as, an acknowledgement or any form of suggestion that this prior art forms parts of the common general knowledge in any country.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

What is claimed is:

1. A wearable defibrillator system, comprising:
   a support structure configured to be worn by a patient;
   an energy storage module configured to store a charge;
   two electrodes coupled with the support structure and configured to be applied to two respective patient locations of the patient;
   a reservoir coupled to the support structure and configured to store a fluid;
   a fluid deploying mechanism configured to cause at least some of the fluid to be released from the reservoir and be deployed near at least one of the patient locations, so as to cause an impedance between the two electrodes to be decreased; and
   an impedance measurement circuit configured to sense the decreased impedance, and
   in which the stored charge is delivered to the patient locations via the electrodes after the sensed impedance meets a discharge condition, and
   the fluid releasing mechanism is caused to release some more of the fluid, if the impedance is sensed to be above a second threshold.

2. The system of claim 1, further comprising:
   a processor configured to cause the stored charge to be delivered, when the discharge condition is met.

3. The system of claim 1, in which
   the reservoir includes an exit mechanism that has a directing tube.

4. The system of claim 1, in which
   the fluid deploying mechanism includes a pump configured to pump the fluid out of the reservoir.

5. The system of claim 1, in which
   an ECG measurement is taken via the electrodes.

6. The system of claim 1, in which
   the discharge condition is that the sensed impedance has a value below a first threshold.

7. The system of claim 6, in which
   a determination is made that the charge needs to be delivered, and
   the first threshold has a first value if the needed delivery of the charge is appropriate for a first electrical therapy, and
   the first threshold has a second value different from the first value if the needed delivery of the charge is appropriate for a second electrical therapy.

8. The system of claim 7, in which
   the first electrical therapy is defibrillation and the second electrical therapy is pacing.

9. The system of claim 1, in which
   the discharge condition is that the sensed impedance has a value that changes less than a threshold in a given amount of time.

10. The system of claim 1, in which
    the discharge condition is that a timeout threshold has lapsed, since causing at least some of the fluid to be released.

11. The system of claim 1, further comprising:
    a user interface configured to output an alert if the sensed impedance decreases below an alert threshold.

12. The system of claim 1, further comprising:
    a memory, and
    in which a time profile of the sensed impedance is stored in the memory.

13. A non-transitory computer-readable storage medium storing one or more programs which, when executed by a defibrillator system including an energy storage module, an impedance measurement circuit, two electrodes configured to be applied to two respective patient locations of a patient, a reservoir containing fluid, and a fluid deploying mechanism, they result in operations comprising:
storing a charge;
causing at least some of the fluid to be released from the reservoir and be deployed near at least one of the patient locations, so as to cause an impedance between the two electrodes to be decreased;
sensing the decreased impedance; and
causing the charge to be delivered to the patient locations via the electrodes after the sensed impedance meets a discharge condition, and
in which the fluid releasing mechanism is caused to release some more of the fluid, if the impedance is sensed to be above a second threshold.

14. The medium of claim 13, in which executing the one or more programs further results in:
taking an ECG measurement via the electrodes.

15. The medium of claim 13, in which executing the one or more programs further results in:
the discharge condition is that the sensed impedance has a value below a first threshold.

16. The medium of claim 15, in which executing the one or more programs further results in:
making a determination that the charge needs to be delivered, and in which
the first threshold has a first value if the needed delivery of the charge is appropriate for a first electrical therapy, and
the first threshold has a second value different from the first value if the needed delivery of the charge is appropriate for a second electrical therapy.

17. The medium of claim 16, in which
the first electrical therapy is defibrillation and the second electrical therapy is pacing.

18. The medium of claim 13, in which executing the one or more programs further results in:
the discharge condition is that the sensed impedance has a value that changes less than a threshold in a given amount of time.

19. The medium of claim 13, in which
the discharge condition is that a timeout threshold has lapsed, since causing at least some of the fluid to be released.

20. The medium of claim 13, in which executing the one or more programs further results in:
outputting an alert if the sensed impedance decreases below an alert threshold.

21. The medium of claim 13, in which
a time profile of the sensed impedance is stored in a memory.

22. A method for a defibrillator system including an energy storage module, an impedance measurement circuit, two electrodes configured to be applied to two respective patient locations of a patient, a reservoir containing fluid, and a fluid deploying mechanism, the method comprising:
storing a charge;
causing at least some of the fluid to be released from the reservoir and be deployed near at least one of the patient locations, so as to cause an impedance between the two electrodes to be decreased;
sensing the decreased impedance; and
causing the charge to be delivered to the patient locations via the electrodes after the sensed impedance meets a discharge condition, and
in which the fluid releasing mechanism is caused to release some more of the fluid, if the impedance is sensed to be above a second threshold.

23. The method of claim 22, further comprising:
taking an ECG measurement via the electrodes.

24. The method of claim 22, in which
causing the at least some of the fluid to be released and be deployed includes pumping the fluid.

25. The method of claim 22, in which
the discharge condition is that the sensed impedance has a value below a first threshold.

26. The method of claim 25, further comprising:
making a determination that the charge needs to be delivered, and in which
the first threshold has a first value if the needed delivery of the charge is appropriate for a first electrical therapy, and
the first threshold has a second value different from the first value if the needed delivery of the charge is appropriate for a second electrical therapy.

27. The method of claim 26, in which
the first electrical therapy is defibrillation and the second electrical therapy is pacing.

28. The method of claim 22, further comprising:
the discharge condition is that the sensed impedance has a value that changes less than a threshold in a given amount of time.

29. The method of claim 22, in which
the discharge condition is that a timeout threshold has lapsed, since causing at least some of the fluid to be released.

30. The method of claim 22, further comprising:
outputting an alert if the sensed impedance decreases below an alert threshold.

31. The method of claim 22, in which
a time profile of the sensed impedance is stored in a memory.

* * * * *